(12) United States Patent
Ritter et al.

(10) Patent No.: US 8,268,739 B2
(45) Date of Patent: Sep. 18, 2012

(54) X-RAY OPAQUE BARIUM-FREE GLASSES AND USES THEREOF

(75) Inventors: Simone Monika Ritter, Mainz (DE); Oliver Hochrein, Mainz (DE); Sabine Pichler-Wilhelm, Landshut (DE)

(73) Assignee: Schott AG, Mainz (DE)

( * ) Notice: Subject to any disclaimer, the term of this patent is extended or adjusted under 35 U.S.C. 154(b) by 227 days.

(21) Appl. No.: 12/695,419

(22) Filed: Jan. 28, 2010

(65) Prior Publication Data

US 2010/0210755 A1 Aug. 19, 2010

(30) Foreign Application Priority Data

Feb. 13, 2009 (DE) .................. 10 2009 008 953

(51) Int. Cl.
*C03C 3/15* (2006.01)
*C03C 3/155* (2006.01)
*C03C 3/112* (2006.01)

(52) U.S. Cl. .................. 501/50; 501/51; 501/57
(58) Field of Classification Search .................. 501/57, 501/50, 51
See application file for complete search history.

(56) References Cited

U.S. PATENT DOCUMENTS

| | | | |
|---|---|---|---|
| 3,529,946 A | 9/1970 | Fischer et al. | |
| 4,472,030 A | 9/1984 | Tachibana et al. | |
| 5,132,254 A | 7/1992 | Stempin et al. | |
| 5,641,347 A * | 6/1997 | Grabowski et al. | 106/35 |
| 5,827,790 A | 10/1998 | Evans et al. | |
| 5,976,999 A | 11/1999 | Evans et al. | |
| 6,297,181 B1 * | 10/2001 | Kunert et al. | 501/57 |
| 6,677,046 B2 | 1/2004 | Hachitani et al. | |
| 6,716,779 B2 | 4/2004 | Lin | |
| 6,816,319 B2 | 11/2004 | Tsuda et al. | |
| 7,399,721 B2 * | 7/2008 | Koyo et al. | 501/65 |
| 2002/0157570 A1 * | 10/2002 | Brodkin et al. | 106/35 |
| 2003/0045421 A1 * | 3/2003 | Burger et al. | 501/41 |
| 2003/0161048 A1 | 8/2003 | Tsuda et al. | |
| 2006/0264313 A1 | 11/2006 | Fechner et al. | |
| 2007/0042894 A1 | 2/2007 | Aitken et al. | |
| 2007/0122356 A1 | 5/2007 | Kessler et al. | |
| 2008/0096752 A1 | 4/2008 | Nagaoka | |
| 2008/0153068 A1 | 6/2008 | Kessler et al. | |
| 2008/0213495 A1 | 9/2008 | Miyauchi et al. | |
| 2008/0254965 A1 * | 10/2008 | Ishioka | 501/64 |
| 2008/0255265 A1 * | 10/2008 | Hoescheler et al. | 523/117 |

FOREIGN PATENT DOCUMENTS

| | | |
|---|---|---|
| DE | 35 01 898 | 4/1988 |
| DE | 35 24 605 | 6/1990 |
| DE | 41 00 604 | 2/1992 |
| DE | 40 29 230 | 3/1992 |
| DE | 44 43 173 | 7/1996 |
| DE | 198 49 388 | 5/2000 |
| DE | 100 63 939 | 7/2002 |
| DE | 102 22 964 | 7/2004 |
| DE | 10 2004 026 433 | 12/2005 |
| DE | 10 2005 019 958 | 2/2006 |
| DE | 10 2006 012 116 | 9/2007 |
| DE | 603 15 684 | 6/2008 |
| EP | 0 634 373 | 1/1995 |
| EP | 0 885 606 | 5/1998 |
| EP | 997132 A1 * | 5/2000 |
| EP | 1 547 572 | 6/2005 |
| EP | 1953122 | 8/2008 |
| GB | 1 440 172 | 6/1976 |
| GB | 2 232 988 | 1/1991 |
| JP | 60-221338 | * 11/1985 |
| JP | 62-012633 | 1/1987 |
| JP | 2000-159540 | 6/2000 |
| JP | 2002-243543 | 8/2002 |
| JP | 2004-516260 | 6/2004 |
| JP | 2004516260 | 6/2004 |
| JP | 2006-052125 | 2/2006 |
| JP | 2007-515450 | 6/2007 |
| JP | 2007515450 | 6/2007 |
| WO | 2005/060921 | 7/2005 |
| WO | 2005/080283 | 9/2005 |
| WO | 20071077680 | 7/2007 |
| WO | WO-2007/077680 | 7/2007 |
| WO | 2007/104300 | 9/2007 |
| WO | 2008/123378 | 10/2008 |

* cited by examiner

*Primary Examiner* — James J Seidleck
*Assistant Examiner* — Peter A Salamon
(74) *Attorney, Agent, or Firm* — Pearl Cohen Zedek Latzer, LLP

(57) ABSTRACT

Zirconium-containing BaO- and PbO-free X-ray opaque glasses having a refractive index $n_d$ of about 1.57 to about 1.61 and a high X-ray opacity with an aluminum equivalent thickness of at least about 400% are provided. Such glasses are based on a $SiO_2$—$Al_2O_3$—$La_2O_3$—$ZrO_2$—$Cs_2O$ system with additions of $Li_2O$, $Na_2O$, ZnO and/or $Ta_2O_5$. Such glasses may be used, in particular, as dental glasses or as optical glasses.

26 Claims, No Drawings

X-RAY OPAQUE BARIUM-FREE GLASSES AND USES THEREOF

RELATED APPLICATION

This application claims priority to and benefit of German Application No. 10 2009 008 953.5 filed on Feb. 13, 2009, the contents of which are hereby incorporated by reference in their entirety.

FIELD OF THE INVENTION

The present invention relates to barium- and lead-free X-ray opaque glasses and to uses thereof.

BACKGROUND OF THE INVENTION

Plastic dental compositions are increasingly being used for dental restoration in the dental sector. Such plastic dental compositions usually include a matrix of organic resins and various inorganic fillers. Inorganic fillers predominantly comprise powders of glasses, (glass-) ceramics, quartz or other crystalline substances (e.g. $YbF_3$), sol-gel materials or aerosils, which are added to the plastic composition as filling material.

The use of plastic dental compositions is intended to avoid possible harmful side-effects of amalgam and to achieve an improved aesthetic impression. Depending on the plastic dental compositions selected, they can be used for different dental restoration purposes, for example, for tooth fillings, as well as for securing parts, such as crowns, bridges and inlays, onlays etc.

The filling material per se is intended to minimize the shrinkage caused by polymerization of the resin matrix during curing. For example, if there is a strong adhesion between the tooth wall and filling, excessive polymerization shrinkage can lead to the tooth wall breaking. If the adhesion is inadequate, excessive polymerization shrinkage may result in the formation of peripheral gaps between the tooth wall and filling, which can promote secondary caries. Furthermore, certain physical and chemical demands are imposed on the fillers.

It is desirable to process the filling material to form powders that are as fine as possible. The finer the powder, the more homogenous the appearance of the filling. At the same time, the polishing properties of the filling are improved, which in addition to reducing the surface area available for attack also leads to improved resistance to abrasion and therefore to a longer-lasting filling. To enable the powders to be processed successfully, it is also desirable for the powders not to agglomerate. This undesirable effect tends to occur with filling materials produced using sol-gel processes.

Furthermore, it is advantageous if filler particles are coated or at least partially coated with functionalized silane, since this facilitates formulation of dental compositions and improves the mechanical properties.

Furthermore, the refractive index and color of the entire plastic dental composition, including fillers, should be as well matched as possible to the natural tooth material, so that it is as indistinguishable as possible from the surrounding, healthy tooth material. The grain size of the pulverized filler being as small as possible also helps to achieve this aesthetic criterion.

It is also important for the thermal expansion of the plastic dental composition in the typical range of use, i.e. usually between −30° C. and +70° C., to be matched to that of the natural tooth material in order to ensure that dental restoration measures are sufficiently able to withstand temperature changes. Excessively high stresses caused by temperature changes also can cause formation of gaps between plastic dental compositions and the surrounding tooth material, which in turn can form sites of attack for secondary caries. In general, fillers with the lowest possible coefficient of thermal expansion are used to compensate for the high thermal expansion of the resin matrix.

Good chemical resistance of the fillers with respect to acids, alkalis and water and good mechanical stability under load, such as, for example, during movement produced by chewing, can also contribute to a long service life for dental restoration measures.

Furthermore, for the treatment of patients, it is imperative that dental restoration measures can be seen in an X-ray image. Since the resin matrix itself is generally invisible in an X-ray image, the fillers must provide the required X-ray absorption. A filler of this type which provides sufficient absorption of X-radiation is described as X-ray opaque. Constituents of fillers, for example, certain components of a glass, or other substances, are generally responsible for X-ray opacity. Such substances are often referred to as X-ray opacifiers. A standard X-ray opacifier is $YbF_3$, which can be added to the filler in crystalline, milled form.

According to International Standard DIN ISO 4049, the X-ray opacity of dental glasses or materials is quoted in relation to the X-ray absorption of aluminum as aluminum equivalent thickness (ALET). The ALET is the thickness of an aluminum sample which has the same absorption as a 2 mm-thick sample of the material to be tested. An ALET of 200% therefore means that a small glass plate having plane-parallel surfaces and a thickness of 2 mm produces the same X-ray attenuation as a small aluminum plate with a thickness of 4 mm. Analogously, an ALET of 150% means that a small glass plate having plane-parallel surfaces and a thickness of 2 mm produces the same X-ray attenuation as a small aluminum plate with a thickness of 3 mm.

Because plastic dental compositions in use are usually introduced into cavities from cartridges and then modeled in the cavities, such compositions should be at least somewhat thixotropic in the uncured state. This means that viscosity decreases when pressure is exerted, while it is dimensionally stable without the action of pressure.

Among plastic dental compositions, a distinction also should be drawn between dental cements and composites. In the case of dental cements, also known as glass ionomer cements, the chemical reaction of fillers with the resin matrix leads to curing of the dental composition and consequently the curing properties of the dental composition. Thus, their workability is influenced by the reactivity of the fillers. This often involves a setting process which is preceded by a radical surface curing, for example, under the action of UV light. Composites, also referred to as filling composites, contain by contrast fillers which are as chemically inert as possible, since their curing properties are determined by constituents of the resin matrix itself and a chemical reaction of the fillers often disrupts this.

Because glasses, due to their different compositions, represent a class of materials with a wide range of properties, they are often used as fillers for plastic dental compositions. Other applications as dental material, either in pure form or as a component of a material mixture, are also possible, for example, for inlays, onlays, facing material for crowns and bridges, material for artificial teeth or other material for prosthetic, preservative and/or preventive dental treatment. Glasses of this type used as dental material are generally referred to as dental glasses.

In addition to the dental glass properties described above, it is also desirable for this glass to be free from barium and/or barium oxide (BaO), which are classified as harmful to health, and also from lead and/or lead oxide (PbO) and from other barium and lead compounds.

In addition, it is also desirable for a component of dental glasses to be zirconium oxide ($ZrO_2$). $ZrO_2$ is a widely-used material in the technical fields of dentistry and optics. $ZrO_2$ is readily biocompatible and is distinguished by its insensitivity to temperature fluctuations. It is used in a wide variety of dental supplies in the form of crowns, bridges, inlays, attachment work and implants.

Dental glasses therefore represent glasses of particularly high quality. Glasses of this type also can be used in optical applications, particularly if such applications benefit from the X-ray opacity of the glass. Since X-ray opacity means that the glass absorbs electromagnetic radiation in the region of the X-ray spectrum, corresponding glasses simultaneously act as filters for X-radiation. Sensitive electronic components can be damaged by X-radiation. In the case of electronic image sensors, for example, the passage of an X-ray quantum may damage the corresponding region of the sensor or result in an undesirable sensor signal which can be perceived, for example, as an image disturbance and/or disturbing pixels. For specific applications it is therefore necessary, or at least advantageous, to protect electronic components against X-radiation by using corresponding glasses to filter said components out from the spectrum of the incident radiation.

A number of dental glasses and optical glasses are known from the prior art.

For example, DE10063939 describes a dental glass which is used, for example, in self-curing dental cement compositions. This glass reacts with acids and releases ions which serve to build up a network to facilitate curing. This is an undesirable property, however, for composites which are cured using UV light. In addition, the total content of $Y_2O_3$, $La_2O_3$ and other lanthanoids is 30 to 70% by weight, which provides a refractive index above 1.61.

EP1547572 describes a glass filler material for epoxy systems and the production thereof. The particles described therein have a particle size of 0.1 μm up to 20 μm and comprise an inner and an outer zone which have different alkali metal concentrations and in which the alkali metal ions of the inner layer do not migrate into the outer layer during the period of use. The depletion of the outer layer takes place in a further step, after the melted glass has been milled, by adding an organic or inorganic acid which is subsequently washed out again. Glass powder produced in this way has a refractive index ($n_d$) of 1.49 to 1.55. In order that the alkali metal ions can be leached out, the molten glass must have a low chemical resistance.

WO2007077680 describes radiation shielding glass having a high lanthanide content of at least 20 mol %. This contributes to refractive indexes ($n_d$) of all glasses obtained in this way to be beyond the use range of aesthetic composite materials, the maximum refractive indexes ($n_d$) of which are typically around 1.60.

US20070042894 describes a substrate for flat screens which consists of (60-80 mol %) $SiO_2$, (5-25 mol %) $Al_2O_3$ and (2-5 mol %) elements from the group of rare earth oxides. In addition, the glass may contain up to 15 mol % of network-modifying elements selected from the following group: MgO, SrO, BaO, CaO, $B_2O_3$, $Ta_2O_5$, $TiO_2$, $ZrO_2$, $HfO_2$, $SnO_2$, $P_2O_5$, ZnO, SbO, $As_2O_3$ or SnO up to 20 mol %. The described glass is distinguished by particularly high melting temperatures in order to make it possible to achieve high process temperatures of at least 650° C. The substrate glass described herein does not contain any elements from the group of alkali metals ($Li_2O$, $Na_2O$, $K_2O$, $Rb_2O$, $Cs_2O$) and cannot be processed in a cost-effective manner.

U.S. Pat. No. 6,816,319 describes a planar lens consisting of a flat glass substrate into which a refractive-index-increasing component diffuses, which results in a gradient of the refractive index within the lens. A non-homogeneous refractive index has a strong negative effect on the optical impression of the finished restoration.

U.S. Pat. No. 6,677,046 describes a glass ceramic used as a substrate for LCD displays. However, the material obtained must contain a beta-quartz phase which is obtained by subsequent heat treatment. Differences in the refractive index of the crystalline phase and of the residual glass phase make it impossible to produce a highly aesthetic filling.

U.S. Pat. No. 6,716,779 describes a glass substrate for interference filters having a relatively high coefficient of thermal expansion. This adapted coefficient of thermal expansion means that $Al_2O_3$ is limited to no more than 12 mol %. Particularly in $B_2O_3$-free glasses (which represent most of the examples in this reference) $Al_2O_3$ reduces the coefficient of expansion resulting in poor chemical resistance.

JP2000159540 describes certain aluminum borosilicate glass used for substrates in information storage technology. The glass described therein contains $B_2O_3$ which impairs the chemical resistance of the glass to an unacceptable extent and therefore is not suitable for dental glasses.

GB2232988 describes certain alkali-resistant glass fiber material which contains at least 8 mol % $ZrO_2$. This high content results in poor melting properties and a tendency to form a Tyndall effect.

Features common to the glasses mentioned in the prior art are that they either (1) have a relatively high refractive index $n_d$, and/or (2) have low weathering resistance and/or (3) are not X-ray opaque and/or (4) in addition are often difficult or expensive to produce and/or (5) contain components which are harmful to the environment and/or to health.

SUMMARY OF THE INVENTION

An object of the invention is to provide barium- and lead-free X-ray opaque glasses having a relatively low refractive index $n_d$ of about 1.57 to about 1.61. Such glasses should be suitable as dental glass and as optical glass, should be inexpensive to produce, but nevertheless have a high quality and be tolerated by the body, should be suitable for passive and active tooth protection and should have excellent properties with regard to processability, setting behavior of surrounding plastic matrices and long-term stability and strength. In addition, a further object of the invention is that of ensuring that glasses according to the present invention are extremely resistant to weathering.

Such glasses also should have an ALET of at least about 400% and may include (in % by weight based on oxide) $SiO_2$ 43-53, $Al_2O_3$ 15-21, $Li_2O$ 0-6, $Na_2O$ 0-2, $K_2O$ 0-2, $Cs_2O$ 0.5-7, ZnO 0-6, $ZrO_2$ 3-10, $La_2O_3$ 13-<20, $Ta_2O_5$ 0-5, Σ alkali metal oxides 3.5-9.

The basic matrix of a glass according to the present invention usually should be free from color-imparting components such as, for example, $Fe_2O_3$, AgO, CuO etc., in order to permit an optimum color locus and therefore adaptation to the tooth color and, in the case of optical applications, the spectrum of the electromagnetic radiation passing through.

DETAILED DESCRIPTION OF THE INVENTION

Glasses according to the present invention have a refractive index $n_d$ of about 1.57 to about 1.61. Such glasses match very well to the available dental plastics and/or epoxy resins in this refractive index range, as a result of which they effectively satisfy the aesthetic demands placed on a dental glass/plastic composite in terms of natural appearance.

Glasses according to the invention achieve the properties of barium- and/or lead-containing dental glasses in terms of the required X-ray absorption without the use of barium and/or lead or other substances harmful to health or classed accordingly. X-ray absorption and therefore X-ray opacity are achieved mainly by the $CsO_2$ and/or $La_2O_3$ content; these are present in glasses according to the invention in an amount greater than about 10% by weight, either alone or in combination. Both $CsO_2$ and $La_2O_3$ are regarded as harmless to health.

Glasses according to the invention also have an ALET of at least about 400%. This means that a small glass plate which is made from glasses according to the invention and has plane-parallel surfaces and a thickness of 2 mm produces the same X-ray attenuation as a small aluminum plate with a thickness of 8 mm.

In certain embodiments glasses according to the present invention contain $SiO_2$ in a proportion of about 43 to less than about 53% by weight as a glass-forming component. Higher $SiO_2$ contents can lead to disadvantageously high melting temperatures as well as inadequate X-ray opacity.

Certain embodiments of the present invention provide an $SiO_2$ content of about 44 to less than about 52% by weight and particularly preferably of 44 to 51% by weight. The lower limit of about 51% by weight reduces the tendency for devitrification.

Glasses according to the invention also may contain $ZrO_2$ in a proportion of more than about 3 to at most about 10% by weight. This zirconium content improves to a surprising degree the mechanical properties, in particular, tensile and compressive strength, and reduces the brittleness of such glasses. In addition, this component promotes X-ray opacity of the glass. In certain embodiments, $ZrO_2$ content may be from about 3 to about 9% by weight, and in other embodiments preferably from about 4 to about 8% by weight.

In addition, it has been discovered that a ratio of $SiO_2$ and $ZrO_2$ content greater than or at least equal to 7 should be maintained, since $ZrO_2$ is sparingly soluble in silicate glasses and therefore segregation can easily occur. The segregated regions act as centers for scattering light that passes through, analogous to the Tyndall effect. In the case of dental glasses, these centers of scattering impair the aesthetic impression, and therefore segregated glasses are not acceptable for dental applications. In an optical glass, the centers of scattering generally have an adverse effect on transmission, and so segregated glasses are also undesirable in most optical applications.

Glasses according to the invention also may contain $Al_2O_3$ in a range from about 15 to less than about 21% by weight. Among other things, $Al_2O_3$ provides good chemical resistance. However, an $Al_2O_3$ content of about 21% by weight should not be exceeded in order to avoid increasing the viscosity of the glass, particularly in the hot-processing range, to such an extent that it is difficult to melt the glass. Contents of higher than about 21% by weight are also disadvantageous for the melting of $ZrO_2$-containing glass. In certain embodiments, glasses according to the invention preferably contain from about 16 to about 20% by weight $Al_2O_3$, and in other embodiments preferably from about 17 to about 20% by weight.

Glasses according to the present invention may contain from 0 to about 6% by weight ZnO and from 0 to about 5% by weight $Ta_2O_5$. ZnO may reduce the coefficient of thermal expansion and has a positive effect on the chemical resistance to water and acids. Therefore, in certain embodiments of the present invention ZnO may be present from about 1 to about 5% by weight, and in other embodiments from about 2 to about 4% by weight. $Ta_2O_5$ may contribute both to setting a desirable refractive index and in promoting X-ray opacity. Therefore in certain embodiments of the present invention $Ta_2O_5$ may be present from about 1 to about 4% by weight, and in other embodiments from about 1.5 to about 3.5% by weight.

In order to make it easier to melt glasses according to the present invention, the sum total of alkali metal oxides present in such glasses may be from at least about 3.5% by weight to at most about 9% by weight. However, alkali metal oxides may reduce the chemical resistance of a glass. The total content of alkali metal oxides in certain embodiments is preferably from about 3.5 to about 8% by weight and in other embodiments preferably from about 4 to about 8% by weight.

Individually, the content of the alkali metal oxides in glasses according to the present invention may be from 0 to about 6% by weight $Li_2O$, 0 to about 2% by weight $Na_2O$, 0 to about 2% by weight $K_2O$ and about 0.5 to about 7% by weight $Cs_2O$.

$K_2O$ promotes, to a certain extent, improved melting of $SiO_2$- and $ZrO_2$-containing glasses. Certain embodiments of the present invention may contain from 0 to about 1.5% by weight $K_2O$, and in certain embodiments preferably from 0 to about 1% by weight $K_2O$.

In certain embodiments the $Li_2O$ content may be from about 1 to about 5% by weight, and in other embodiments from about 2 to about 5% by weight.

Glasses according to the present invention are also preferably free from $CeO_2$.

$Cs_2O$ also may improve melting properties, while simultaneously serving to promote X-ray opacity and to set the refractive index. In certain embodiments of the present invention the $Cs_2O$ content may be from about 1 to about 6% by weight, and in other embodiments from about 2 to about 5% by weight.

Glasses according to the present invention also may contain from about 13 up to about 20% by weight $La_2O_3$ itself. As already described, $La_2O_3$, possibly together with $Cs_2O$ and/or $ZrO_2$, contributes to X-ray opacity of the glass. In certain embodiments the $La_2O_3$ content is may be from about 13.5 up to about 20% by weight, and in other embodiments from about 14 to about 19% by weight.

In order to achieve high X-ray opacity and correspondingly high values of ALET, certain embodiments of the present invention provide for the sum total of $Cs_2O$ and/or $La_2O_3$ present in the glass to be from about 14 to about 25% by weight, in other embodiments from about 15 to about 24% by weight, and in other embodiments preferably from about 16 to about 24% by weight.

In certain embodiments of the present invention $WO_3$, $Nb_2O_5$, $HfO_2$, $Ta_2O_5$, $Gd_2O_3$, $Sc_2O_3$, $Y_2O_3$ and/or $SnO_2$ may be present alone or in combination in amounts from 0 to about 3% by weight in each case.

According to certain embodiments of the invention from 0 to about 2% by weight of $SnO_2$ may optionally be present as well.

As already described, glasses according to the invention should be free from barium and/or lead and BaO and/or PbO which are harmful to the environment or are classified as harmful to health. The addition of other substances harmful to the environment and/or classified as harmful to health is preferably avoided. In particular, certain embodiments of the invention also do not contain SrO because SrO is likewise not accepted in applications relating to health.

Embodiments of the present invention also provide glasses which are preferably free from other components not mentioned in the claims and/or in the present description, i.e. according to such embodiments, the glass consists essentially of the components mentioned. The expression "consists essentially of" here means that other components are present, at most, as impurities, but are not deliberately added to the glass composition as individual components.

However, the invention also provides for the use of glasses according to the invention as a basis for further glasses, in which up to about 5% by weight of further components can be added to glasses according to the invention. In such cases, glasses may consist of at least about 95% by weight of glasses according to the invention.

All of the glasses according to the invention are noted for surprisingly good chemical resistance, which results in a high degree of unreactivity in cooperation with the resin matrix and thus provides a very long service life of dental compositions.

In embodiments of the present invention it is also possible to adapt the color appearance of the glass by adding oxides customary for this purpose. Oxides suitable for imparting color to glasses are known to a person skilled in the art; examples which may be mentioned are CuO and CoO which, for this purpose, can preferably be added in such embodiments in amounts from 0 to about 0.1% by weight.

The present invention also includes glass powders made from glasses according to the invention. Such glass powders may be produced by known processes, such as, for example, those described in DE 41 00 604 C1. Glass powders according to certain embodiments of the invention preferably have a mean grain size of up to about 40 µm, and in other embodiments preferably up to about 20 µm. In other embodiments nanopowders having mean grain sizes of 50 to 400 nm are preferred. Other grain sizes and/or grain size distributions are also encompassed by the invention. The above-mentioned glass powder can generally serve as starting material for the use of glasses according to the invention as fillers and/or dental glasses.

In another embodiment of the invention, the surface of glass powder is silanized using conventional methods. Silanization allows the bonding of the inorganic fillers to the plastic matrix of the plastic dental composition to be improved.

As already described, glasses according to the present invention may be used as dental glass. Such glasses may be employed as fillers in composites for dental restoration, particularly for those based on epoxy resin which require such fillers to be substantially chemically inert. It is also within the scope of the invention for glasses according to the invention to be used as an X-ray opacifier in dental compositions. Such glasses are suitable for replacing expensive crystalline X-ray opacifiers, such as, for example $YbF_3$.

Accordingly, the present invention also includes dental glass/plastic composites which contain glasses described herein in the form of dental glass. In certain embodiments the dental glass is in the form of glass powders. The dental plastic may be a UV-curable resin based on acrylate, methacrylate, 2,2-bis[4-(3-methacryloxy-2-hydroxypropoxy)phenyl]propane (bis-GMA), urethane methacrylate, alkanediol dimethacrylate or cyanoacrylate.

The present invention also includes optical elements which contain glasses described herein. Optical elements are understood to encompass components which can be used for a wide variety of optical applications. These include components through which light passes. Examples of such components include cover glasses and/or lens elements, in addition to carriers of other components, such as, for example, mirrors and glass fibers.

Cover glasses may be used to protect electronic components which include optoelectronic components. Cover glasses are usually present in the form of glass plates having plane-parallel surfaces and are preferably fitted above the electronic component, such that the latter is protected against environmental effects while allowing electromagnetic radiation, such as light, to pass through the cover glass and interact with the electronic component. Examples of such cover glasses include optical caps, elements for the protection of electronic image sensors, cover wafers in wafer level packaging, cover glasses for photovoltaic cells and protective glasses for organic electronic components. Further applications for cover glasses are well known to a person skilled in the art. It is also possible for optical functions to be integrated in the cover glass, for example, when the cover glass is provided at least in regions with optical structures which may preferably be in the form of lenses. Cover glasses provided with microlenses are often used as cover glasses for image sensors of digital cameras, the microlenses usually focusing light impinging obliquely on the image sensor onto the individual sensor elements (pixels).

Since glasses according to embodiments of the present invention are substantially chemically inert, they may be suitable for applications such as substrate glass in photovoltaics, both for covering silicon-based photovoltaic cells and organic photovoltaic cells and as carrier material of thin-film photovoltaic modules. X-ray absorption of glasses according to the invention have, inter alia, particular advantages when employing photovoltaic modules in space travel, since the latter can be exposed to particularly intense X-radiation outside the Earth's atmosphere.

Glasses according to the present invention are also suitable for use as substrate glass for biochemical applications, in particular for molecular screening processes.

In other embodiments the high thermal stability of glasses according to the invention allows them to be suitable as lamp glass, in particular for use in halogen lamps. If the light generation mechanisms in the lamp produce X-radiation, a particular advantage of glasses according to the invention is that they can keep the X-radiation away from the surroundings.

In addition, embodiments of the invention include the evaporation of glasses described herein by means of physical processes and the deposition of evaporated glass on certain components. Such physical vapor deposition processes (PVD processes) are known to a person skilled in the art and are described, for example, in DE 102 22 964 B4. Here, glasses according to the present invention serve as targets to be evaporated in such processes. Components which are evaporation-coated with glasses according to the invention can benefit both from the chemical resistance of the glass and from X-ray absorption thereof.

It is also possible for embodiments of the present invention to be used as starting material for glass fibers. The term "glass fiber" encompasses all types of glass fibers, in particular fibers comprising only a core, and so-called core-shell fibers having a core and at least one shell which preferably completely surrounds the core along the outer circumferential surface. Glasses according to the present invention may be used as core glass and/or as shell glass. Within the composition range of glasses according to the invention, the refractive index $n_d$ of the glass can be set such that a core glass according to the invention has a higher refractive index than a shell glass according to the invention, forming a so-called step-index fiber in which light is conducted very efficiently by total reflection at the core-shell interface.

Because of its good chemical resistance, glass fibers according to the present invention may be used as reinforcements in composite materials and/or as reinforcements for concrete and/or as optical fibers embedded in concrete.

Examples 1-4

Table 1 below provides 4 representative embodiments of the present invention labeled Example 1 through Example 4. All quantitative descriptions of the particular components of these embodiments are given in % by weight (based on oxide).

Glasses described in these Examples were produced as follows:

The raw materials for the oxides were weighed out without refining agents and then thoroughly mixed. The glass batch was melted down at about 1580° C. in a batchwise melting unit, then refined and homogenized. The glass may be poured at a temperature of about 1600° C. as ribbons or with other desired dimensions, and processed. The temperatures may be reduced by at least about 100 K in a large-volume, continuous unit.

For further processing, the cooled glass ribbons were milled with the aid of the process described in DE 41 00 604 C1, the contents of which are incorporated by reference herein, to form a glass powder with a mean grain size of about 10 μm or less. The glass properties were determined on the basis of glass gobs which had not been milled into powders. All of these glasses have excellent chemical resistance with respect to acids, alkalis and water. In addition, they are very chemically inert.

Table 1 also lists the refractive indexes $n_d$, the coefficients of linear thermal expansion $\alpha_{(20-300°\ C.)}$ from 20 to 300° C. and $\alpha_{(-30-70°\ C.)}$ from −30 to 70° C. The latter is of particular interest when glasses according to the invention are used as dental glass because the temperature range from −30 to 70° C. can occur during use.

Table 1 also lists the aluminum equivalent thickness (ALET) and the chemical resistance of each of the Examples provided therein. In Table 1 SR represents the acid resistance class according to ISO8424, AR represents the alkali resistance class according to ISO10629 and HGB represents the hydrolytic resistance class according to DIN ISO719.

All of the glasses listed in Table 1 have coefficients of thermal expansion a in the range from 20 to 300° C. of less than $6\cdot10^{-6}$/K.

Glasses shown in Table 1 have an X-ray opacity which is at least as good as that of glasses containing BaO and SrO. In the Examples shown, ALET values of 597% to 801% were obtained. Example No. 3 shows the highest X-ray absorption value and the highest ALET value. In this Example, the total content of $La_2O_3$ and $Cs_2O$ is 26.23% by weight, and is therefore the highest.

A feature common to all of these Examples listed in Table 1 is that their chemical resistance can be classed in the best SR, AR and HGB classes 1 or 1.0, such that these glasses are therefore very suitable for the uses mentioned.

The Examples also demonstrate that the refractive indexes $n_d$ of glasses according to the invention may be adapted to the intended application within an appropriate range around 1.6, without adversely affecting the outstanding chemical resistance. As a result, such glasses may be advantageously used in particular as fillers in dental compositions and for other applications which impose high demands, inter alia, on purity, chemical resistance and thermal stability. Such glasses also may be produced on a large industrial scale at a reasonable cost.

Compared to the prior art, glasses according to the invention have the further advantage that they link the adaptability of the refractive indexes and coefficients of expansion and provide surprisingly good chemical stability with efficient X-ray absorption.

In addition, glasses according to the present invention are surprisingly easy to melt and therefore can be produced at a reasonable cost.

TABLE 1

Compositions of X-ray opaque glass in % by weight

| Example | 1 | 2 | 3 | 4 |
|---|---|---|---|---|
| $SiO_2$ | 49.78 | 46.71 | 45.96 | 45.38 |
| $Al_2O_3$ | 19.08 | 18.18 | 17.89 | 17.67 |
| $Li_2O$ | 4.09 | 3.22 | 2.75 | 3.43 |
| $Na_2O$ | | | 1.50 | |
| $K_2O$ | | 0.81 | | |
| $Cs_2O$ | 1.82 | 1.21 | 3.41 | 3.37 |
| ZnO | 3.37 | 3.51 | 2.96 | 2.97 |
| $La_2O_3$ | 14.3 | 17.63 | 16.56 | 19.86 |
| $ZrO_2$ | 4.99 | 6.27 | 6.02 | 4.48 |
| $Ta_2O_5$ | 2.57 | 2.45 | 2.94 | 2.90 |
| $n_d$ | 1.57938 | 1.59508 | 1.5926 | 1.5962 |
| $\alpha_{(20-300°\ C.)}$ [$10^{-6}$/K] | 5.26 | 5.24 | 5.5 | 5.57 |
| $\alpha_{(-30,\ 70°\ C.)}$ [$10^{-6}$/K] | 4.25 | 4.21 | 4.49 | 4.53 |
| ALET [%] | 597 | 712 | 762 | 801 |
| SR [class] | 1.0 | 1.0 | 1.0 | 1.0 |
| AR [class] | 1.0 | 1.0 | 1.0 | 1.0 |
| HGB [class] | 1 | 1 | 1 | 1 |

What is claimed is:

1. A BaO— and/or PbO-free X-ray opaque glass comprising (in % by weight based on oxide)

| | |
|---|---|
| $SiO_2$ | 43-53 |
| $Al_2O_3$ | 15-21 |
| $Li_2O$ | 0-6 |
| $Na_2O$ | 0-2 |
| $K_2O$ | 0-2 |
| $Cs_2O$ | 0.5-7 |
| ZnO | 0-6 |
| $ZrO_2$ | 3-10 |
| $La_2O_3$ | 13-<20 |
| $Ta_2O_5$ | 0-5 |
| Σ alkali metal oxides | 3.5-9 | wherein the X-ray opaque glass is free of BaO and/or PbO, has a refractive index $n_d$ of about 1.57 to about 1.61 and an aluminum equivalent thickness of at least about 400%.

2. The glass of claim 1, comprising

| | |
|---|---|
| $SiO_2$ | 44-52 |
| $Al_2O_3$ | 16-20 |
| $Li_2O$ | 1-5 |
| $K_2O$ | 0-1.5 |
| $Cs_2O$ | 1-6 |
| ZnO | 1-5 |
| $ZrO_2$ | 3-9 |
| $La_2O_3$ | 13.5-<20 |
| $Ta_2O_5$ | 1-4 |
| Σ alkali metal oxides | 3.5-8. |

3. The glass of claim 1, comprising

| | |
|---|---|
| $SiO_2$ | 44-51 |
| $Al_2O_3$ | 17-20 |
| $Li_2O$ | 2-5 |
| $K_2O$ | 0-1 |
| $Cs_2O$ | 2-5 |
| ZnO | 2-4 |
| $ZrO_2$ | 4-8 |
| $La_2O_3$ | 14-19 |
| $Ta_2O_3$ | 1.5-3.5 |
| Σ alkali metal oxides | 4-8. |

4. The glass of claim 1, wherein the sum total of the $Cs_2O$ and/or $La_2O_3$ content is between about 14% and about 25%.

5. The glass of claim 1, wherein the ratio of the $SiO_2$ and $ZrO_2$ contents is:
$SiO_2/ZrO_2 \geq 7$.

6. The glass of claim 1, further comprising

| | |
|---|---|
| $WO_3$ | 0-3 |
| $Nb_2O_5$ | 0-3 |
| $HfO_2$ | 0-3 |
| $Ta_2O_5$ | 0-3 |
| $Gd_2O_3$ | 0-3 |
| $Sc_2O_3$ | 0-3 |
| $Y_2O_3$ | 0-3 |
| $SnO_2$ | 0-2. |

7. The glass of claim 1, wherein said glass is free from SrO.

8. A glass comprising at least 95% (in % by weight based on oxide) of the glass of claim 1.

9. A glass powder comprising the glass of claim 1.

10. The glass powder of claim 9, wherein the surfaces of the powder grains are silanized.

11. A dental glass/plastic composite comprising the glass powder of claim 9.

12. An optical element comprising the glass of claim 1.

13. A dental glass comprising the glass of claim 1.

14. A filler in composites for dental restoration comprising the glass of claim 1.

15. A dental glass/plastic composite comprising the glass of claim 1, wherein said dental plastic comprises a UV-curable resin based on acrylate, methacrylate, 2,2-bis[4-(3-methacryloxy-2-hydroxypropoxy)phenyl]propane (bis-GMA), urethane methacrylate, alkanediol dimethacrylate or cyanoacrylate.

16. An X-ray opacifier in plastic dental compositions comprising the glass of claim 1.

17. An optical device comprising the glass of claim 1.

18. A cover glass for an electronic component comprising the glass of claim 1.

19. The cover glass of claim 18, wherein the electronic component is a sensor.

20. A display device comprising the glass of claim 1.

21. A substrate glass in a photovoltaic device comprising the glass of claim 1.

22. A substrate glass and/or cover glass in an OLED device comprising the glass of claim 1.

23. A lamp glass comprising the glass of claim 1.

24. A substrate glass for biomedical devices comprising the glass of claim 1.

25. A target material for PVD processes comprising the glass of claim 1.

26. A glass fiber comprising core glass and/or shell glass, wherein said core glass and/or shell glass comprises the glass of claim 1.

* * * * *